US008338346B2

(12) United States Patent
Diersing et al.

(10) Patent No.: US 8,338,346 B2
(45) Date of Patent: Dec. 25, 2012

(54) PERFUME COMPOSITIONS COMPRISING FUNCTIONAL PERFUME COMPONENTS

(75) Inventors: Steven Louis Diersing, Cincinnati, OH (US); Ricky Ah-Man Woo, Hamilton, OH (US); Rhonda Jean Jackson, Cincinnati, OH (US); Zaiyou Liu, West Chester, OH (US); Ronald David Turner, Elsmere, KY (US); Fernando Ray Tollens, Cincinnati, OH (US); LaVar Duran Derrick, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 350 days.

(21) Appl. No.: 12/533,075

(22) Filed: Jul. 31, 2009

(65) Prior Publication Data
US 2010/0028289 A1 Feb. 4, 2010

Related U.S. Application Data

(60) Provisional application No. 61/085,641, filed on Aug. 1, 2008.

(51) Int. Cl.
*C11D 3/50* (2006.01)
*A61K 8/37* (2006.01)
(52) U.S. Cl. ............ 510/107; 510/102; 512/21; 512/26; 512/2
(58) Field of Classification Search .............. 512/1, 26, 512/21, 2; 510/107, 102
See application file for complete search history.

(56) References Cited

U.S. PATENT DOCUMENTS

| 4,561,997 A | 12/1985 | Roehl |
| 4,649,046 A | 3/1987 | Kross |
| 4,671,959 A | 6/1987 | Warren et al. |
| 4,956,342 A | 9/1990 | Christenson et al. |
| 6,583,106 B2 * | 6/2003 | Zofchak ............... 512/2 |
| 2009/0253612 A1 | 10/2009 | Mushock et al. |
| 2012/0039753 A1 * | 2/2012 | Diersing et al. ........... 422/123 |

FOREIGN PATENT DOCUMENTS

| EP | 0 177 255 A2 | 4/1986 |
| EP | 0 695 552 A1 | 2/1996 |
| GB | 2 260 494 A | 4/1993 |
| WO | WO 89/08462 A1 | 9/1989 |
| WO | WO 00/05948 A1 | 2/2000 |
| WO | WO 03/033038 A1 | 4/2003 |

OTHER PUBLICATIONS

PCT International Search Report, Mailed Feb. 11, 2010, 5 Pages.

* cited by examiner

*Primary Examiner* — Douglas McGinty
(74) *Attorney, Agent, or Firm* — Amy I Ahn-Roll

(57) ABSTRACT

Perfume compositions having functional perfume components for aiding in perfume evaporation. The functional perfume components have a Kovat's index in the range of 900-1400 and an ODT of greater than about 1 ppb. In one embodiment, the functional perfume component may be present in an amount from at least about 10% by weight of the composition. In another embodiment, the composition containing a function perfume component is substantially free of a VOC.

15 Claims, 2 Drawing Sheets

PERFUME COMPOSITIONS COMPRISING FUNCTIONAL PERFUME COMPONENTS

CROSS-REFERENCES TO RELATED APPLICATIONS

This application claims priority under 35 U.S.C. §119(e) to U.S. Provisional Application Ser. No. 61/085,641 filed Aug. 1, 2008.

FIELD OF THE INVENTION

The present invention relates to perfume compositions having functional perfume components for aiding evaporation of non-functional perfume components without compromising the intended perfume character of the composition.

BACKGROUND OF THE INVENTION

Various perfume compositions are available to mask, deodorize, and/or remove malodors in the air. These compositions may be dispensed by air freshening systems, including electric plug-in diffuser, passive diffusers, trigger spray dispensers, and aerosol dispensers. In many instances, adequate delivery of perfume compositions into the air requires the use of evaporation or dispensing aids.

Plug-in air fresheners, for example, may utilize liquid compositions containing 20% or more volatile organic compounds ("VOCs") as a perfume evaporation aid. "VOCs" as used herein means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether.

In liquid electric plug-in air fresheners, DPM and MMB are commonly used. In aerosol dispensers, a commonly used dispensing aid or propellant is hydrocarbon, which is a VOC. The Environmental Protection Agency and California Air Resource Board ("CARB") currently regulate some VOCs. Currently regulated VOCs, classified by CARB regulations, can be found in Article 2, §94508(a)(144) of the California Consumer Products Regulation. Given such regulations and the desire to protect the environment, approaches for reducing VOC content is desirable.

One approach in reducing the VOC content in such aerosol air sanitizers is to simply reduce the content of VOCs. However, a reduction in VOC content can adversely affect product performance. Specifically, in a liquid electric plug-in air freshener, VOCs may aid in keeping perfume components in solution which aids in evaporation profiles of the composition as it diffuses from the plug-in device. As such, reducing the VOC level may compromise the delivery of an intended perfume character. Reducing the propellant content in an aerosol dispenser may result in excessive product remaining in the dispenser at the end of its life. It may also increase the particle size of the dispensed product which can lead to excessive surface deposition.

Another approach for reducing VOC content, which is specific to aerosol dispensers, is outlined in U.S. Pat. No. 7,014,127. This approach utilizes at most 25% of a liquefied gas propellant free of butane, in combination with a specific range of can pressures and valve orifice dimensions.

There remains a need for compositions, including air freshening compositions, having components that solubilize perfume and/or aid in perfume evaporation without compromising the intended perfume character of the composition and without, or with a reduced level of, VOCs.

SUMMARY OF THE INVENTION

The present invention is directed to a composition having an active agent, a non-functional perfume component, and greater than about 10%, by weight of the composition, of a functional perfume component ("FPC"). The FPC may have a Kovat's index from about 900 to about 1400 and an odor detection threshold ("ODT") equal to or greater than about 1.0 parts per billion ("ppb").

The present invention is also directed to an air freshening composition that is substantially free of VOCs and comprises from greater than about 10%, by weight of the composition, of a FPC selected from the group consisting of: iso-nonyl acetate, dihydro myrcenol, linalool, d-limonene, and combinations thereof.

The present invention is further directed to a method of modulating perfume evaporation comprising the step of providing a composition having a non-functional perfume component and from greater than about 10% by weight of the composition, of a FPC having a Kovat's index in the range of 900-1400 and an ODT equal to or greater than about 1.0 ppb.

DETAILED DESCRIPTION OF THE INVENTION

Figure 1:
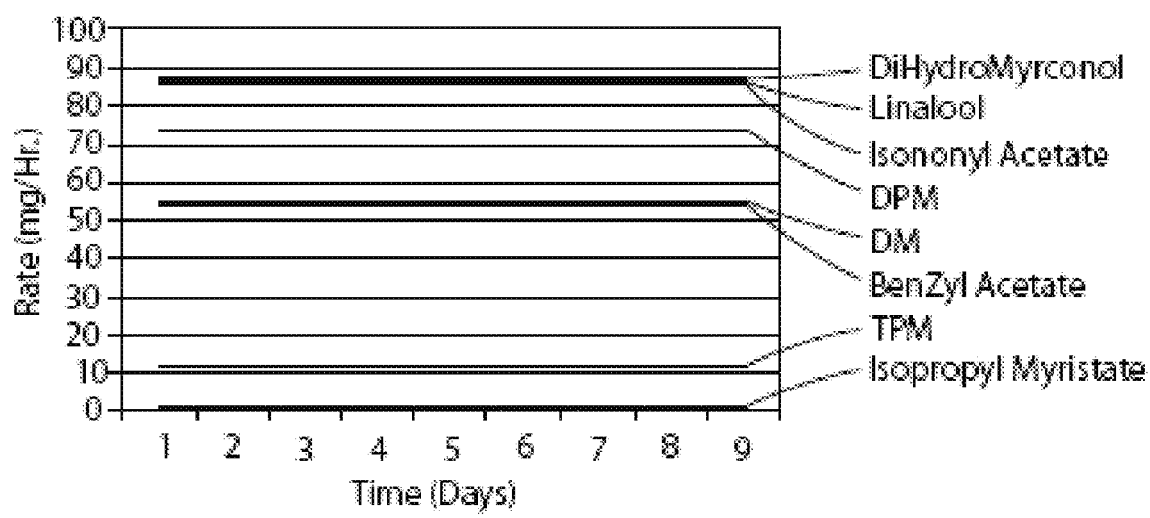
FIG. 1 is a line graph illustrating the evaporation profile of certain FPCs, according to the present invention, compared to traditional organic solvents used in air freshening compositions.

The present invention is directed to a composition having an active agent, a non-functional perfume component, and a FPC. The FPC may have a Kovat's index from about 900 to about 1400 and an ODT of greater than about 1.0 ppb. The present invention eliminates or reduces the need for ingredients or materials that have VOCs that are able to aid in perfume evaporation. "VOCs" as used herein means volatile organic compounds that have a vapor pressure of greater than 0.2 mm Hg measured at 20° C. and aid in perfume evaporation.

FPCs

The FPCs of the present invention are a class of perfume raw materials with evaporation properties that are similar to traditional organic solvents or VOCs commonly used in air freshening compositions. FPCs aid in the evaporation of perfume raw materials. In some embodiments, FPCs may provide a secondary fragrance benefit. In such embodiments, at least one perfume raw material that is not a FPC will be present to provide the hedonic benefits of the composition. FPCs may be used in relatively large concentrations without negatively impacting perfume character of the composition.

It has been understood that perfume raw material generates an olfactory response in the individual smelling the perfume. The minimum concentration of perfume ingredient which is consistently perceived to generate an olfactory response in an individual is known as the ODT. As the concentration of perfume is increased, so are the odor intensity of the perfume and the olfactory response of the individual. This continues until the concentration of the perfume reaches a maximum, at which point the odor intensity reaches a plateau beyond which there is no additional olfactory response by the individual. This range of perfume concentration through which the individual consistently perceives an odor is known as the Odor Detection Range ("ODR"). The concentration of perfume raw materials in a composition should be formulated at the ODT or within the ODR of the perfume raw materials, since compositions comprising higher levels are costly and inefficient.

The Applicants have, however, found that in some circumstances it may be desirable to utilize FPCs that exceed the ODT, alternatively that exceed the ODR. Specifically, the use of these FPCs at higher levels than traditionally used in air freshening compositions surprisingly aids in evaporation of non-functional perfume components or perfume components that are included for their fragrance. Further, the use of these FPCs does not interfere with the perfume characteristics of the non-functional perfume components that are included for their fragrance or hedonic benefits.

The properties of the perfume raw materials that make them suitable as a FPC can be defined using any of the following physical chemical properties: flashpoint, vapor pressure, Kovat's Index, boiling point, molecular weight, heat of vaporization, and combinations of these and other physical chemical properties. The chosen perfume raw materials for use in this application can also be defined using ODT and non-polarizing scent character for a given perfume character scent camp.

A suitable FPC may have an ODT from greater than about 1.0 ppb, alternatively greater than about 5.0 ppb, alternatively greater than about 10.0 ppb, alternatively greater than about 20.0 ppb, alternatively greater than about 30.0 ppb, alternatively greater than about 0.1 parts per million ("ppm").

ODTs may be determined using a commercial gas chromatograph ("GC") equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability.

The necessary amount of analyte is injected onto the column to achieve a 50 ppb concentration at the detector. Typical gas chromatograph parameters for determining odor detection thresholds are listed below. The test is conducted according to the guidelines associated with the equipment.

Equipment:
   GC: 5890 Series with FID detector (Agilent Technologies, Ind., Palo Alto, Calif., USA)
   7673 Autosampler (Agilent Technologies, Ind., Palo Alto, Calif., USA)
   Column: DB-1 (Agilent Technologies, Ind., Palo Alto, Calif., USA)
   Length 30 meters ID 0.25 mm film thickness 1 micron (a polymer layer on the inner wall of the capillary tubing, which provide selective partitioning for separations to occur)

Method Parameters:
   Split Injection: 17/1 split ratio
   Autosampler: 1.13 microliters per injection
   Column Flow: 1.10 mL/minute
   Air Flow: 345 mL/minute
   Inlet Temp. 245° C.
   Detector Temp. 285° C.
   Temperature Information
   Initial Temperature: 50° C.
   Rate: 5 C/minute
   Final Temperature: 280° C.
   Final Time: 6 minutes
   Leading assumptions: (i) 12 seconds per sniff
      (ii) GC air adds to sample dilution Suitable FPCs may be highly volatile, low boiling, perfume ingredients. Non-limiting, suitable FPCs include iso-nonyl acetate, dihydro myrcenol (3-methylene-7-methyl octan-7-ol), linalool (3-hydroxy-3,7-dimethyl-1,6 octadiene), geraniol (3,7 dimethyl-2,6-octadien-1-ol), d-limonene (1-methyl-4-isopropenyl-1-cyclohexene, benzyl acetate, isopropyl mystristate, and combinations thereof. Table 1 lists the approximate reported values for exemplary properties of certain FPCs. FIG. 1 shows the evaporation profile of certain FPCs in relation to commonly used VOCs in air freshening compositions.

TABLE 1

| FPC | Boiling Point (° C.) | MW | Clog P @ 25° C. | Flash point (° C.) | Vapor pressure | Kovat's Index | ODT |
|---|---|---|---|---|---|---|---|
| Iso-Nonyl Acetate (CAS 58430-94-7) | 224.72 | 186.3 | 4.28 | 79.4 | 0.11 | 1178 | 12 ppb |
| Dihydro Myrcenol (CAS18479-58-8) | 197.66 | 156.3 | 3.03 | 76.1 | 0.1 | 1071 | 32 ppb |
| Linalool (CAS 78-70-6) | 205.1 | 154.3 | 2.549 | 78.9 | 0.05 | 1107 | 22 ppb |
| Geraniol (CAS 106-24-1) | 237.4 | 154.3 | 2.769 | 100 | 0.00519 | 1253 | 0.4 ppb |
| D-Limonene (CAS 94266-47-4) | 169.7 | 136 | 4.35 | 47.2 | 1.86 | 1034 | 204 ppb |

It is believed that a single FPC can be used alone or in combination with other FPCs without negatively distorting the intended perfume character. The total FPC content, by weight, in a composition may be greater than about 10%, alternatively greater than about 15%, alternatively greater than about 20%, alternatively greater than about 25%, alternatively greater than about 30%, alternatively greater than about 35%, alternatively greater than about 40%, alternatively greater than about 45%, alternatively greater than about 50%, alternatively from about 10% to about 95%, alternatively from about 15% to about 95%, alternatively from about 20% to about 95%, alternatively from about 20% to about 95%, alternatively from about 25% to about 95%, alternatively from about 30% to about 95%, alternatively from about 35% to about 95%, alternatively from about 40% to about 95%, alternatively from about 45% to about 95%, alternatively from about 50% to about 95%, by weight of the composition.

Use of FPCs at the recited levels may help modulate the evaporation profile of an entire perfume composition to provide perfume character consistency over the intended usage period in various system including personal care products such as skin moisturizers, body deodorants, facial and body cleansers, baby wipes; surface care compositions such as hard surface cleaners, wood polishes, and automobile cleaners; fabric care compositions such as cleaners, softeners, de-wrinklers, and refreshers; air care products such as air freshener systems including aerosols, electric plug-in diffusers, passive diffusers, coupled and decoupled piezoelectric systems, wick based systems, gel matrixes; etc. For purposes of illustrating the present invention in further detail, compositions having FPCs for a liquid electric plug-in air freshener are described. The terms "air freshening composition" or "air freshener", as used herein, refer to any suitable composition that reduces odors in air, and/or reduces the impression of odors in the air by masking, layering or including malodor counteractant perfume raw materials into the composition. This is one of many embodiments of the present invention and is not to limit the full scope of the invention as stated in the claims.

Numerous types of air freshening compositions are possible. Using liquid compositions for plug-in air fresheners as a non-limiting example, the suitable FPCs may have a Kovat's index in the range from about 800 to about 1500; alternatively from about 900 to about 1400; alternatively from about 1000 to about 1300. These materials can be either an ether, an alcohol, an aldehyde, an acetate, a ketone, or mixtures thereof. Non-limiting FPC combinations, or binary FPC compositions, include those listed in Table 2.

TABLE 2

Iso Nonyl Acetate + Linalool for a Watery type fragrance
Geraniol + D Limonene for a Floral type fragrance
Dihydro Myrcenol + Iso-Nonyl Acetate + Linolool for a Gourmand type Fragrance
Iso-Nonyl Acetate – Universal application for all scent types Non-Functional Perfume Component The composition of the present invention includes a non-functional perfume component or components, which are traditional perfume raw materials that are utilized for their fragrance, scent, or hedonic benefits. Non-functional perfume components do not satisfy the properties of an FPC. Suitable non-functional perfume components are disclosed in U.S. Pat. Nos. 5,663,134; 5,670,475; 5,783,544; 5,939,060; and 6,146,621.

Active Agent

The present invention may also include an active agent, which is any agent that provides cleaning, surface care protection, fabric conditioning or softening, fabric refreshing, de-wrinkling, air freshening, air deodorizing, malodor removal, skin moisturizing, body deodorizing, or like benefits. An active agent does not include water or deionized water.

In an air freshening or fabric refreshing composition, the active agents may deliver a genuine malodor removal benefit. A genuine malodor removal benefit is defined as both a sensory and analytically measurable (such as by GC) malodor reduction. Thus, if the air freshening composition delivers a genuine malodor removal benefit, the air freshening composition will not function merely by using perfume to cover up or mask odors. If the air freshening product is provided with a malodor counteractant, the air freshening product may utilize one or more of several types of odor control mechanisms. One suitable malodor controlling agent is cyclodextrin, which is disclosed in U.S. Pat. Nos. 5,534,165; 5,668,097; 5,714,317; and 6,682,694.

Active agents might also include surfactants, emulisifiers, solubilizers, polymers, malodor counteractants such as cyclodextrin, hydrogen peroxide, buffers, zinc ions, etc. For example, suitable fabric conditioning/softening agents are disclosed in U.S. Pat. No. 5,139,687.

In one embodiment, the composition is substantially free of VOCs and has no more than about 18%, by weight of the composition, of VOCs. In another embodiment, the composition is substantially free of VOCs and has no more than about 6%, by weight of the composition, of VOCs. In yet another embodiment, the composition is substantially free of VOCs and has no more than about 5%, by weight of the composition, of VOCs. In yet another embodiment, the composition is substantially free of VOCs and has no more than about 1%, by weight of the composition, of VOCs. In yet another embodiment, the composition is substantially free of VOCs and has no more than about 0.5%, by weight of the composition, of VOCs. In yet another embodiment, the composition is free of VOCs.

Table 3 is provided for purposes of illustrating exemplary perfume compositions which may be used in a liquid electric plug-in air freshener. In accordance with the present invention, Compositions A1, A2, A3, and A4 include FPCs without the presence of VOCs.

TABLE 3

| Floral Type | | | |
|---|---|---|---|
| Perfume Raw Material | KI Value | Composition A1 | Composition B1 |
| Phenyl Hexanol | 1509 | 2 | 2 |
| Cis-3-Hexenyl Acetate | 1002 | 1 | 1 |
| Beta Gamma Hexanol | 851 | 1.5 | 1.5 |
| Benzyl Acetate | 1164 | 8.5 | 3.5 |
| Benzyl Propionate | 1258 | 5 | 2 |
| Iso Nonyl Acetate | 1178 | 20 | — |
| Dihydro Myrcenol | 1071 | 12 | 3 |
| Hydroxycitronellal | 1286 | 5 | 5 |
| Geraniol | 1253 | 10 | 2 |
| Citronellol | 1227 | 10 | 5 |
| Linalool | 1107 | 7 | 7 |
| Phenyl Ethyl Alcohol | 1121 | 3.5 | 3.5 |
| Methyl Dihydro Jasmonate | 1705 | 5 | 5 |
| Hexyl Cinnamic Aldehyde | 1760 | 2 | 2 |
| Lyral | 1670 | 3 | 3 |
| Lillial | 1538 | 4 | 4 |
| Phenyl Ethyl Phenyl Acetate | 1932 | 0.5 | 0.5 |
| VOC | | | |
| MMB | | | 15 |
| DPM | | | 35 |
| Total | | 100% | 100% |

TABLE 3-continued

Outdoor Type

| Perfume Raw Material | KI Value | Composition A2 | Composition B2 |
|---|---|---|---|
| Hexyl Acetate | 1008 | 15 | 10 |
| Cis-3-Hexenyl Acetate | 1002 | 2 | 2 |
| Beta Gamma Hexanol | 851 | 1.5 | 1.5 |
| Prenyl Acetate | 918 | 2 | 2 |
| Ligustral | 1097 | 1.5 | 1.5 |
| Melonal | 1060 | 3 | 3 |
| Eucalyptol | 1047 | 2.5 | 2.5 |
| Undecavertol | 1265 | 7 | 7 |
| Ethyl-2-Methyl Butyrate | 845 | 2 | 2 |
| Nerol | 1229 | 10 | 5 |
| Citral | 1271 | 3 | 3 |
| Citronellal Nitrile | 1223 | 8 | 8 |
| Decyl Aldehyde | 1204 | 1.5 | 1.5 |
| Octyl Aldehyde | 1000 | 1.5 | 1.5 |
| Methyl Nonyl Acetaldehyde | 1366 | 0.2 | 0.2 |
| Lauric Aldehyde | 1408 | 0.5 | 0.5 |
| Iso Nonyl Acetate | | 22 | — |
| Verdox | 1310 | 12 | 12 |
| Methyl Dihydro Jasmonate | 1705 | 4.8 | 4.8 |
| VOC | | | |
| MMB | | | 32 |
| DPM | | | |
| Total | | 100% | 100% |

Watery Type

| Perfume Raw Material | KI Value | Composition A3 | Composition B3 |
|---|---|---|---|
| Adoxal | 1510 | 3 | 3 |
| Hydroxycitronellal | 1286 | 12 | 12 |
| Calone 1951 | 1412 | 1.5 | 1.5 |
| Helional | 1572 | 7 | 6 |
| Dimethyl Benzyl Carbinol | 1167 | 8 | 5 |
| Linalool | 1107 | 15 | 15 |
| Iso Nonyl Acetate | 1178 | 20 | — |
| Citral | 1271 | 0.5 | 0.5 |
| Methyl Dihydro Jasmonate | 1705 | 8 | 8 |
| Citronellal Nitrile | 1223 | 8 | 4 |
| Dihydro Myrcenol | 1071 | 12 | 8 |
| Orange Terpenes | 1034 | 5 | 2 |
| VOC | | | |
| MMB | | | 35 |
| DPM | | | |
| Total | | 100% | 100% |

Gourmand Type

| Perfume Raw Material | KI Value | Composition A4 | Composition B4 |
|---|---|---|---|
| Benzyl Acetate | 1164 | 6 | 3 |
| Nonalactone | 1364 | 5 | 3 |
| Methyl Dihydro Jasmonate | 1705 | 8 | 8 |
| Linalool | 1106 | 15 | 3 |
| Gamma Undecalactone | 1577 | 4 | 2.5 |
| LRG 201 | 1716 | 1 | 1 |
| Ethyl Vanillin | 1457 | 3.5 | 3.5 |
| Ethyl Maltol | 1123 | 3.5 | 3.5 |
| Decyl Aldehyde | 1204 | 1.5 | 1.5 |
| Orange Terpenes | 1034 | 5 | 3 |
| Melonal | 1060 | 2 | 2 |
| Eugenol | 1361 | 1.5 | 1 |
| Cinnamic Alcohol | 1306 | 1.5 | 1.5 |

TABLE 3-continued

| Iso Nonyl Acetate | 1178 | 17.5 | — |
|---|---|---|---|
| Verdox | 1319 | 7 | 7 |
| Ethylene Brassylate | 2040 | 4 | 4 |
| Ambrettolide | 1958 | 0.5 | 0.5 |
| Iso E Super | 1686 | 7 | 7 |
| Bacdanol | 1565 | 5 | 5 |
| Vetiver | 1819 | 1.5 | 1.5 |
| VOCs | | | |
| MMB | | | 30 |
| DPM | | | 8.5 |
| Total | | 100% | 100% |

Example

Sensory and evaporation rate measurements are conducted on a representative perfume composition containing FPCs, as in Table 4 and in accordance with the present invention, and a comparable perfume composition using DPM and/or MMB. Two perfume compositions, Perfume Composition A and Perfume Composition B, are made in accordance with Table 4 and are placed in a liquid electric plug-in refill, each refill being identical to one another. The refills are inserted into a liquid electric plug-in device, each device being identical to one another. The liquid electric plug-in devices and their refills are plugged into a multi-outlet rack. Voltage is measure and recorded. At day six, record total refill weight (includes perfume, bottle, wick, wick seal, snap ring). Approximately 24 hours afterwards, on day 7, record total refill weight again. Evaporation rate is calculated per the following formula:

$$\frac{\text{Weight, gms}_1 - \text{Weight, gms}_2 \times 1000}{\text{Time in hours}} = \text{mg/hr,}$$

evaporation rate of perfume per hour 1000 is factor to get to milligrams

Figure 2:
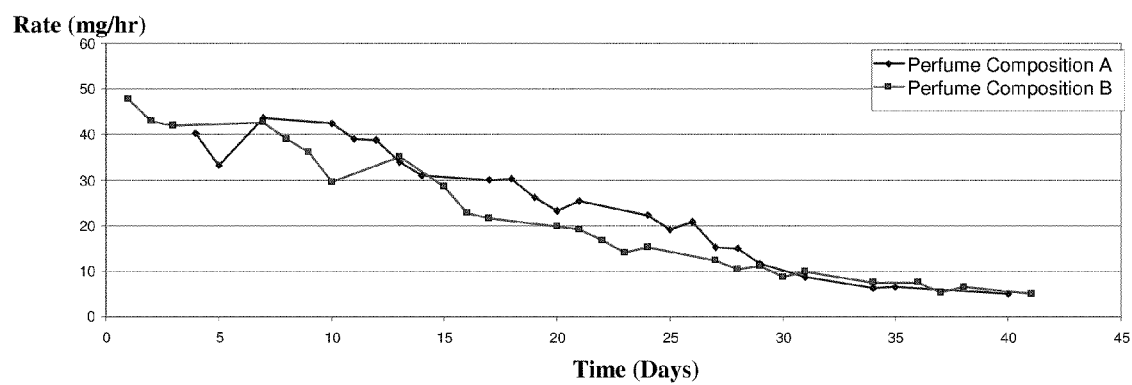
FIG. 2 is a line graph showing evaporation rates on a perfume composition containing FPCs, in accordance with the present invention (Perfume Composition A), and a comparable perfume composition using DPM and/or MMB (Perfume Composition B).

Similar calculations may be performed for other days such as days 7, 14, 21, and 30 days. The evaporation results are shown in FIG. 2.

TABLE 4

| PRM Functionality | Perfume Composition A | Perfume Composition B |
|---|---|---|
| Esters | 6.8 | 26.8 |
| Alcohols | 22.6 | 56.2 |
| Ketones | 2.1 | 2.1 |
| Aldehydes | 9.9 | 9.9 |
| Terpenes | 4.1 | 4.1 |
| Lactones | 0.3 | 0.3 |
| Musks | 0.6 | 0.6 |
| MMB | 15 | |
| DPM | 37.7 | |
| Total | 100% | 100% |

Direct sensory comparisons between perfume compositions containing DPM and/or MMB versus perfume compositions with FPC substitutions are conducted by trained perfumers and sensory evaluators on days 1 and 21. The sensory comparison results are shown in Table 5.

TABLE 5

| | Day 1 | Day 21 |
|---|---|---|
| Perfume Composition A (Table 4 Composition) | Odor evenly distributed within the evaluation room. Floral, Green, Musky | Odor evenly distributed within the evaluation room. Floral, Green, Musky |
| Perfume Composition B (Table 4 Composition) | Comparable performance to Perfume Composition A: Odor evenly distributed within the evaluation room. Floral, Green, Musky | Comparable performance to Perfume Composition A: Odor evenly distributed within the evaluation room. Floral, Green, Musky |

Both the sensory testing and evaporation rate measurements demonstrate that the FPC's contained in the exemplary compositions above are suitable in place of DPM and/or MMB to aid in perfume evaporation.

In order to under the sensory impact of FPC substitutions on various perfume scent types, additional scent camps are sensory tested, in a liquid electric plug-in air freshener, on perfume compositions that represent key odor types typically found in conventional perfumery (i.e. green watery—top note type, floral—mid note type, and gourmand vanilla type—base note type) utilizing FPC substitutions as singular substitutions and binary FPC compositions to determine scent camp character integrity and odor presentation benefits with FPCs versus compositions using DPM and/or MMB. As such, the perfume compositions include (1) nonfunctional perfume components and (2) FPCs; or (1) nonfunctional perfume components and (2) DPM, or MMB, or both DPM and MMB. Direct sensory comparisons between compositions containing DPM and/or MMB versus compositions with FPC substitutions containing iso-nonyl acetate and/or dihydro myrcenol are conducted by trained perfumers and sensory evaluators. Surprisingly, as shown in Table 7, the odor presentation of the compositions containing the FPC singular components provided increased room diffusion, freshness, and accentuated new elements of the fragrances such as green freshness and fruity freshness versus the composition containing DPM and/or MMB. Even more unexpected, were the results of the binary FPC compositions where the fragrance display was even further enhanced with a more well balanced fragrance presentation, increased fragrance body and fullness, and the highest level of fresh and/or clean odor characteristics. Therefore, iso-nonyl acetate, dihydro myrcenol, linalool, d-limonene, and combinations thereof are suitable in place of VOCs, such as DPM and MMB, to aid in perfume evaporation. More surprisingly, these FPCs enhance the character of the non-functional perfume components and improve room fill.

TABLE 7

| Perfume Composition | Odor Characteristics | Suitable Replacement | Enhanced Perfume Character/ Room Fill |
|---|---|---|---|
| Control Composition 1 - Green Watery type - DPM composition | Green, Fruity, Floral, Slight Chemical base note | Not Applicable | No |
| Green Watery type - Dihydro Myrcenol substitution | Softer, Richer Floral, Fresher, More Diffusive vs. Control Composition 1 | Yes | Yes |
| Green Watery type - Iso Nonyl Acetate substitution | More Fruity, More Green Watery, More Full Bodied vs. Control Composition 1 | Yes | Yes |
| Green Watery type - Binary Dihydro Myrcenol and Iso Nonyl Acetate mixture substitution | Most well balanced presentation, More Full bodied, Fresher, Clean, Excellent room diffusion vs. Control Composition 1 | Yes | Yes |
| Control Composition 2 - Floral type - DPM composition | Floral, Fruity, Green, Powdery, Slight Chemical base note | Not Applicable | No |
| Floral type - Dihydro Myrcenol substitution | Fresher, Richer Floral, More Diffusive and Brighter presentation vs. Control Composition 2 | Yes | Yes |
| Floral type - Iso Nonyl Acetate substitution | More Fruity, More Green, More intense top note presentation, Effervescent vs. Control Composition 2 | Yes | Yes |
| Floral type - Binary Dihydro Myrcenol and Iso Nonyl Acetate mixture substitution | Most well balanced presentation, More full bodied, Fresher, More Complex Floral vs. Control Composition 2 | Yes | Yes |
| Control Composition 3 - Vanilla Gourmand type - DPM and MMB composition | Vanilla, Powdery, Sweet | Not Applicable | No |

TABLE 7-continued

| Perfume Composition | Odor Characteristics | Suitable Replacement | Enhanced Perfume Character/ Room Fill |
|---|---|---|---|
| Vanilla Gourmand type - Dihydro Myrcenol substitution | More Floral, Softer, More Diffusive vs. Control Composition 3 | Yes | Yes |
| Vanilla Gourmand type - Iso Nonyl Acetate substitution | More Fruity, More Top Note Diffusive, Sweeter vs. Control Composition 3 | Yes | Yes |
| Vanilla Gourmand type - Binary Dihydro Myrcenol and Iso Nonyl Acetate mixture substitution | Most well balanced presentation, More Full Bodied, Fresher, More complex sweet and powdery cosmetic quality vs. Control Composition 3 | Yes | Yes |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   an active agent
   a non-functional perfume component;
   a FPC mixture comprising iso-nonyl acetate and a second FPC selected from the group consisting of: dihydro myrcenol, linalool, geraniol, d-limonene, benzyl acetate, isopropyl mystristate, and combinations thereof, wherein said FPC mixture is present in an amount from about 15% to about 95%, by weight of said composition;
   wherein said composition is substantially free of a VOC having a vapor pressure greater than 0.2 mmHg at 20° C.; and
   wherein said composition is selected from the group consisting of an air freshener and a fabric refresher.

2. The composition of claim 1 wherein said FPC mixture is present in an amount from about 30% to about 95% by weight of said composition.

3. The composition of claim 1 wherein said FPC mixture has a Kovat's index from about 800 to about 1500.

4. The composition of claim 1 wherein said FPC mixture has an ODT greater than about 0.1 ppm.

5. The composition of claim 2 wherein said second FPC is selected from the group consisting of dihydro myrcenol, linalool, d-limonene, benzyl acetate, and combinations thereof.

6. An air freshening composition comprising greater than about 10%, by weight, of a FPC mixture comprising iso-nonyl acetate and a second FPC selected from the group consisting of: dihydro myrcenol, linalool, d-limonene, and combinations thereof, wherein said composition is substantially free of a VOC having a vapor pressure greater than 0.2 mm Hg at 20° C.

7. The composition of claim 6 wherein said FPC mixture is present in an amount greater than about 15%, by weight of said composition.

8. The composition of claim 6 wherein said FPC mixture is present in an amount greater than about 20%, by weight of said composition.

9. The composition of claim 6 wherein said FPC mixture is present in an amount greater than about 25%, by weight of said composition.

10. The composition of claim 6 further comprising an active agent selected from the group consisting of surfactants, emulsifiers, solubilizers, polymers, cyclodextrin, hydrogen peroxide, buffers, zinc ions, and mixtures thereof.

11. A method of modulating evaporation of non-functional perfume components comprising the step of providing the composition of claim 1.

12. The method of claim 11 wherein said FPC mixture is present in an amount from greater than about 15% by weight of said composition.

13. The method of claim 12 wherein said FPC mixture is present in an amount from greater than about 30% by weight of said composition.

14. The method of claim 12 wherein said composition further comprises an active agent.

15. The method of claim 12 wherein said composition is substantially free of a VOC having a vapor pressure greater than 0.2 mmHg at 20° C.

* * * * *